(12) United States Patent
Backer et al.

(10) Patent No.: US 9,440,997 B2
(45) Date of Patent: Sep. 13, 2016

(54) HYDROLYSABLE SILANES

(71) Applicant: Dow Corning Corporation, Midland, MI (US)

(72) Inventors: Michael Wolfgang Backer, Mainz (DE); Thomas Chaussee, Fontaines Saint Martin (FR); Sebastien Grofils, Porcheresse (BE); Fabien Rialland, Brussels (BE)

(73) Assignee: DOW CORNING CORPORATION, Midland, MI (US)

( * ) Notice: Subject to any disclaimer, the term of this patent is extended or adjusted under 35 U.S.C. 154(b) by 0 days.

(21) Appl. No.: 14/362,625

(22) PCT Filed: Dec. 7, 2012

(86) PCT No.: PCT/EP2012/074729
§ 371 (c)(1),
(2) Date: Jun. 4, 2014

(87) PCT Pub. No.: WO2013/083742
PCT Pub. Date: Jun. 13, 2013

(65) Prior Publication Data
US 2014/0350277 A1 Nov. 27, 2014

(30) Foreign Application Priority Data

Dec. 8, 2011 (GB) .................. 1121124.0

(51) Int. Cl.
*C07F 7/18* (2006.01)
*C08K 5/548* (2006.01)
*C08C 19/25* (2006.01)

(52) U.S. Cl.
CPC ............. *C07F 7/1836* (2013.01); *C08K 5/548* (2013.01); *C08C 19/25* (2013.01)

(58) Field of Classification Search
CPC ...... C07F 7/1836; C08K 5/548; C08C 19/25
USPC ........................................... 556/423
See application file for complete search history.

(56) References Cited

U.S. PATENT DOCUMENTS

| | | |
|---|---|---|
| 2,853,488 A | 9/1958 | D'Amico et al. |
| 3,147,161 A | 9/1964 | Abere et al. |
| 3,169,122 A | 2/1965 | Hennes |
| 3,379,707 A | 4/1968 | Lund et al. |
| 3,408,198 A | 10/1968 | Reynolds et al. |
| 3,779,703 A | 12/1973 | Tesoro |
| 3,810,843 A | 5/1974 | Slusarczuk et al. |
| 3,855,241 A | 12/1974 | Wilkus et al. |
| 3,928,330 A | 12/1975 | Ramey et al. |
| 4,083,861 A | 4/1978 | Seiler et al. |
| 5,106,680 A | 4/1992 | King et al. |
| 5,369,143 A | 11/1994 | Kurimoto et al. |
| 5,821,277 A | 10/1998 | Hirayama et al. |
| 5,852,099 A | 12/1998 | Vanel |
| 6,494,946 B1 | 12/2002 | Belmont et al. |
| 6,794,428 B2 | 9/2004 | Burrington et al. |
| 6,806,339 B2 | 10/2004 | Cray et al. |
| 7,144,967 B2 | 12/2006 | Sakamoto et al. |
| 7,419,975 B2 | 9/2008 | Palermo et al. |
| 7,732,029 B1 | 6/2010 | Moorlag et al. |
| 7,833,404 B2 | 11/2010 | Matsuda et al. |
| 7,847,117 B2 | 12/2010 | Merget |
| 7,981,966 B2 | 7/2011 | Kobayashi et al. |
| 8,140,294 B2 | 3/2012 | Ramey et al. |
| 8,202,944 B2 | 6/2012 | Suzuki et al. |
| 8,318,858 B2 | 11/2012 | Oshima |
| 8,476,375 B2 | 7/2013 | Backer et al. |
| 8,524,836 B2 | 9/2013 | Kavanagh et al. |
| 8,569,417 B2 | 10/2013 | Backer et al. |
| 2005/0234042 A1 | 10/2005 | Palermo et al. |
| 2010/0056713 A1 | 3/2010 | Oshima |
| 2010/0137499 A1 | 6/2010 | Moorlag et al. |
| 2011/0049056 A1 | 3/2011 | Wyndham et al. |
| 2011/0146877 A1 | 6/2011 | Tanaka et al. |
| 2011/0172367 A1 | 7/2011 | Backer et al. |
| 2012/0059121 A1 | 3/2012 | Backer et al. |
| 2012/0065319 A1 | 3/2012 | Backer et al. |
| 2012/0270997 A1 | 10/2012 | Tanaka et al. |
| 2012/0277369 A1 | 11/2012 | Yoshida et al. |
| 2012/0330044 A1 | 12/2012 | Hou |
| 2013/0079464 A1 | 3/2013 | Nishioka et al. |

FOREIGN PATENT DOCUMENTS

| | | |
|---|---|---|
| DE | 206848 | 2/1984 |
| EP | 2492286 A1 * | 8/2012 |
| GB | 1123303 | 8/1968 |
| GB | 1214451 | 12/1970 |
| GB | 1473335 | 5/1977 |
| HU | 180661 | 4/1983 |
| JP | 5543143 | 3/1980 |
| JP | 10095933 | 4/1998 |
| JP | 2001240706 | 9/2001 |
| JP | 2004085689 | 3/2004 |
| JP | 2004085775 | 3/2004 |
| JP | 2004109586 | 4/2004 |
| JP | 2005249897 | 9/2005 |
| JP | 2008163283 | 7/2008 |

(Continued)

OTHER PUBLICATIONS

Matsuo et al: "Introduction of amino groups into the interlayer space of graphite oxide using 3-aminopropylethoxysilanes", Carbon, Elsevier, Oxford, GB, vol. 45, No. 7, Jun. 1, 2007, pp. 1384-1390.

(Continued)

*Primary Examiner* — Porfirio Nazario Gonzalez
(74) *Attorney, Agent, or Firm* — Matthew T. Fewkes

(57) ABSTRACT

This invention relates to hydrolysable silanes useful in the modification of elastomers, and as coupling agents for diene elastomer compositions containing a filler. In particular the invention relates to novel hydrolysable silanes containing a tertiary amine group and an ether or thioether linkage.

12 Claims, No Drawings

(56) References Cited

FOREIGN PATENT DOCUMENTS

| WO | 9429324 | 12/1994 |
| WO | 0170866 | 9/2001 |
| WO | WO 2011/049180 A1 * | 4/2011 |
| WO | 2011083050 | 7/2011 |

OTHER PUBLICATIONS

Organometallics, vol. 13(9), 1994, (Muehleisen, Mathias; Tacke, Reinhold), pp. 3740-3742.

Russian Journal of Applied Chemistry; vol. 82, Issue 5, pp. 928-930; Journal 2009; by V. M. Farzaliev, M. T. Abbasova, A. A. Ashurova, G. B. Babaeva, N. P. Ladokhina and Ya. M. Kerimova.

The Russian Chemical Bulletin, vol. 44(2), 1995, pp. 374-375.

The Vanderbilt Rubber Handbook (1978), pp. 344 through 346.

Journal of Membrane Science, vol. 129(2), 1997, Barbiou, Mihai et al, pp. 197-207.

European Journal of Organic Chemistry, vol. 13, 2006, (Bianco, Alberto et al.), pp. 2934-2941.

Gasparrini, F. et al., "Molecular recognition of p-tert-butylcalixarenes by surface-linked fullerenes C60 and C70", Tetrahedron, Elsevier Science Publishers, Amsterdam, NL, vol. 57, No. 32, Aug. 6, 2001, pp. 6997-7002.

Bianco et al., "Molecular recognition by a silica-bound fullerene derivative", J. Am. Chem. Soc. 1997, vol. 119, pp. 7550-7554.

Brunauer et al., Adsorption of Gases in Multimolecular Layers, Feb. 1938, pp. 309-319, vol. 60.

Chemische Berichte, vol. 120(4), 1987, Brueckmann, Ralf, et al., pp. 635-641.

* cited by examiner

HYDROLYSABLE SILANES

CROSS REFERENCE TO RELATED APPLICATIONS

This application is a U.S. national stage filing under 35 U.S.C. §371 of PCT Application No. PCT/EP12/74729 filed on 07/DEC/2012, currently pending, which claims the benefit of GB Patent Application No. 1121124.0 filed 08/DEC/2011 under 35 U.S.C. §119 (a)-(d) and 35 U.S.C. §365(a). PCT Application No. PCT/EP12/74729 and GB Patent Application No. 1121124.0 are hereby incorporated by reference.

This invention relates to hydrolysable silanes useful in the modification of elastomers, and as coupling agents for diene elastomer compositions containing a filler. In particular the invention relates to novel hydrolysable silanes containing a tertiary amine group and an ether or thioether linkage.

WO-A-2010/139473 describes various hydrolysable silanes as coupling agents between an inorganic filler and an elastomer. The silanes include those containing an aromatic group having an unsaturated substituent, such as triethoxy (4-vinylphenethyl)silane and 3-(N-styrylmethyl-2-aminoethylamino)propyltriethoxysilane, and those containing a heterocyclic ring such as N-(3-triethoxysilylpropyl)-dihydroimidazole and 1-(3-triethoxysilylpropyl)-pyrrole.

Other examples of hydrolysable silanes which have been proposed as coupling agents include unsaturated silanes containing an ester group, such as an acryloxypropyltrialkoxysilane, described in WO-A-2010/125124.

JP-A-2008-163283 describes a diene synthetic rubber comprising an organosilicon compound and an amine salt.

JP-A-2005-249897 describes compounds of the formula $(R10)_3SiR2NH(R3OR4)$ in which R1 represents a 1-3C alkyl group; R2 represents a 1-8C straight alkylene chain; R3 represents a 1-2C straight alkylene chain; and R4 represents a 1-4C alkyl group. These compounds are used in a resin coating disposed on the surface of magnetic fine powder particles for use as an electrostatic latent image developing carrier.

U.S. Pat. No. 7,847,117 describes alkyl(methoxymethyl) trimethylsilanyl-methylamines of the formula $(R1)_3Si$—C $(R2)_2$-N(R3)-$CH_2$—OR4, where R1 represents methyl or ethyl, R2 represents methyl or hydrogen, R3 represents methyl or hydrogen and R4 represents an alkyl or substituted alkyl group. These are prepared by reacting alkyltrimethylsilanylmethylamines with a substantially equimolar amount of paraformaldehyde and methanol in the presence of a base.

An article in Izvestiya Akademii Nauk, Seriya Khimicheskaya (1995), (2, 382-3 describes the reaction of (R1O) 2RSiCH2NHMe (where R=MeO and R1=Me; or R=EtO and R1=Et; or R=Me and R1=Et) with ClCH2OR2 (R2=Me or Et) in Et2O contg. Et3N to give 40-67% (R1O)2RSiCH2N (Me)CH2OR2.

JP2004-085689 describes a dry imaging material containing a binder which is bridge crosslinked by the crosslinking agent which has a vinyl sulfonyl group, a trimethoxysilyl group, the isocyanate group, or an epoxy group.

JP2004-109586 and JP2004-085775 describe some hydrolysable silanes having tertiary amine group.

DD206848 describes a photographic material containing hydrophilic binder and hardener which is an organo-silicon compound with functional and hydrolysable groups.

The Russian Chemical Bulletin, Volume 44(2), 1995, pages 374-375 describes N-methyl-N-alkoxymethylaminoethyl) dialkoxysilanes.

A hydrolysable silane according to the present invention has the formula:

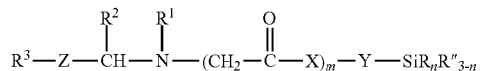

wherein each R represents a hydrolysable group; each R" represents a hydrocarbyl group having 1 to 8 carbon atoms; n=1 to 3; Y represents a divalent organic spacer linkage having 1 to 20 carbon atoms; X represents —O— or NH—; m=0 or 1; $R^1$ represents a hydrocarbyl or substituted hydrocarbyl group having 1 to 20 carbon atoms other than a group of the formula $R^3$—Z—$CH(R^2)$— as defined above; $R^2$ represents hydrogen or a hydrocarbyl or substituted hydrocarbyl group having 1 to 8 carbon atoms; Z represents an oxygen or sulphur atom; and $R^3$ represents a hydrocarbyl or substituted hydrocarbyl group having 1 to 20 carbon atoms, provided that when $R^3$ is CH3, Y has at least 2 carbon atoms.

The hydrolysable silanes of the invention are capable of bonding strongly to diene elastomers under the processing conditions used for producing elastomer products such as tyres. We believe that upon heating to the temperatures used in elastomer processing, the etheramine moiety of the hydrolysable silanes of the invention forms a very reactive species which reacts with the C=C bonds present in diene elastomers through [2+3] cycloaddition. The hydrolysable silanes of the invention are also capable of bonding strongly to fillers having surface hydroxyl groups through hydrolysis of the silane group, thus forming very effective coupling agents.

A process according to the invention for the preparation of a hydrolysable silane of the formula:

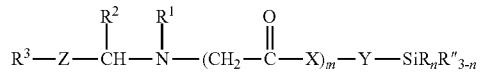

wherein each R represents a hydrolysable group; each R" represents a hydrocarbyl group having 1 to 8 carbon atoms; n=1 to 3; Y represents a divalent organic spacer linkage having 1 to 20 carbon atoms; X represents —O— or NH—; m=0 or 1; $R^1$ represents a hydrocarbyl or substituted hydrocarbyl group having 1 to 20 carbon atoms; $R^2$ represents hydrogen or a hydrocarbyl or substituted hydrocarbyl group having 1 to 8 carbon atoms; Z represents an oxygen or sulphur atom; and $R^3$ represents a hydrocarbyl or substituted hydrocarbyl group having 1 to 20 carbon atoms, is characterised in that a secondary aminoalkylsilane of the formula R'—NH—$(CH_2$—$C(O)$—$X)_m$—Y—$SiR_nR"_{3-n}$ wherein R, R", n, Y, X and $R^1$ are defined as in claim 1, is reacted with an aldehyde of the formula $R^2$—CHO wherein $R^2$ represents hydrogen or a hydrocarbyl or substituted hydrocarbyl group having 1 to 8 carbon atoms and an alcohol or thiol of the formula $R^3ZH$ wherein Z represents an oxygen or sulphur atom; and $R^3$ represents a hydrocarbyl or substituted hydrocarbyl group having 1 to 20 carbon atoms.

Hydrolysable silanes in which a=3 may be preferred as having the maximum number of hydrolysable groups. Examples of groups of the formula $R_aR'_{3-a}Si$-A in which a=3 include trialkoxysilylalkyl groups such as triethoxysilylalkyl or trimethoxysilylalkyl groups, or triacetoxysilylalkyl groups. However hydrolysable silanes in which a=2 or a=1 are also useful coupling agents. In such hydrolysable silanes the group R' is a hydrocarbyl group having 1 to 8 carbon atoms. Preferred groups R' include alkyl groups having 1 to 4 carbon atoms such as methyl or ethyl, but R' can be an alkyl group having more carbon atoms such as hexyl or 2-ethylhexyl or can be an aryl group such as phenyl. Examples of groups of the formula $R_aR'_{3-a}Si-A$ in which a=2 include diethoxymethylsilylalkyl, diethoxyethylsilylalkyl, dimethoxymethylsilylalkyl or diacetoxymethylsilylalkyl groups.

Hydrolysable silanes in which the group R is an ethoxy group are often preferred. The alcohol or acid RH may be released when the silane is hydrolysed, and ethanol the most environmentally friendly compound among the alcohols and acids.

In the group of the formula $-Y-SiR_nR''_{3-n}$, Y represents a divalent organic spacer linkage having 1 to 20 carbon atoms. Preferably Y has 2 to 20 carbon atoms. Y can conveniently be an alkylene group, particularly an alkylene group having 2 to 6 carbon atoms. Preferred examples of linkage Y are $-(CH_2)_3-$, $-(CH_2)_4-$, and $-CH_2CH(CH_3)CH_2-$ groups. The group of the formula $R_aR'_{3-a}Si-A$ can for example be a 3-(triethoxysilyl)propyl, 4-(triethoxysilyl)butyl, 2-methyl-3-(triethoxysilyl)propyl, 3-(trimethoxysilyl)propyl, 3-triacetoxysilylpropyl, 3-(diethoxymethylsilyl)propyl, 3-(diethoxyethylsilyl)propyl or 3-(diacetoxymethylsilyl)propyl group.

The secondary aminoalkylsilane which is reacted with an aldehyde and an alcohol or thiol has the formula $R'-NH-(CH_2-C(O)-X)_m-Y-SiR_nR''_{3-n}$ wherein R, R", n, Y, X are defined as in claim 1 and $R^1$ represents a hydrocarbyl or substituted hydrocarbyl group having 1 to 20 carbon atoms. The group $R^1$ can for example represent a hydrocarbyl group having 1 to 8 carbon atoms. For example the group $R^1$ can be an alkyl group such as $H(CH_2)_{1-8}$, for example a methyl or ethyl group. The group $R^1$ can alternatively be an aryl or aralkyl group, for example a phenyl group or a benzyl group. When m=0, the secondary aminoalkylsilane can for example be $CH_3-NH-(CH_2)_3-Si(OC_2H_5)_3$. Alternatively when m=1, the secondary aminoalkylsilane can for example be $CH3-NH-CH_2-C(O)O-(CH_2)_3-Si(OC_2H_5)_3$ The aldehyde which is reacted with a secondary aminoalkylsilane and an alcohol or thiol has the formula $R^2-CHO$ wherein $R^2$ represents hydrogen or a hydrocarbyl or substituted hydrocarbyl group having 1 to 8 carbon atoms. A preferred aldehyde is formaldehyde, wherein $R^2$ represents hydrogen. The formaldehyde can for example be added to the reaction in the form of paraformaldehyde. Alternative aldehydes include acetaldehyde and butyraldehyde.

In one preferred set of hydrolysable silanes according to the invention, Z represents an oxygen atom and $R^3$ represents a hydrocarbyl group having 1 to 8 carbon atoms. Such silanes can be formed by reaction of an alcohol of the formula $R^3OH$ with a secondary aminoalkylsilane and an aldehyde. Examples of suitable alcohols include ethanol, methanol, propanol, n-butanol, 2-methylpropanol, t-butanol, n-hexanol and 2-ethylhexanol. The alcohol can act as both solvent and reagent in the reaction with the secondary aminoalkylsilane and aldehyde.

The most preferred alcohol is ethanol, i.e. $R^3$ is preferably ethyl. When the hydrolysable silane of the invention reacts with the C=C bonds present in diene elastomers through [2+3] cycloaddition, an alcohol of the formula $R^3OH$ may be liberated. Ethanol is preferred as the most environmentally friendly alcohol.

Examples of this type of hydrolysable silane include:

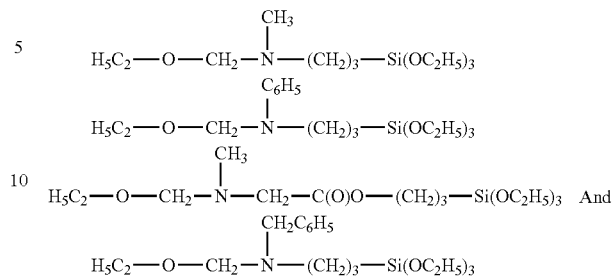

all formed by the reaction of the appropriate secondary aminoalkylsilane with paraformaldehyde in the presence of ethanol as solvent and reagent.

Hydrolysable silanes of the formula:

$$R^3-O-CH_2-\underset{\underset{R^1}{|}}{N}-Y-SiR_nR''_{3-n}$$

can alternatively be prepared by the reaction of a secondary aminoalkylsilane of the formula $R1-NH-(CH_2-C(O)-X)_m-Y-SiR_nR''_{3-n}$ with a chloromethyl ether of the formula $ClCH_2OR^3$ in the presence of a strong organic base such as a trialkylamine in an organic solvent. However this reaction has several disadvantages compared to the preferred reaction using formaldehyde and an alcohol $R^3OH$. Both the base catalyst and the solvent need to be separated from the reaction product, and more by-product is formed. Moreover alcohols and formaldehyde are much more readily available reagents than chloromethyl ethers.

The group $R^1$ can alternatively represent a group of the formula $-Y^*-SiR_qR''_{3-q}$ wherein $Y^*$ represents a divalent organic spacer linkage having 1 to 20 carbon atoms; each R represents a hydrolysable group; each R" represents a hydrocarbyl group having 1 to 8 carbon atoms; and q=1 to 3. The linkage $Y^*$ can be the same as or different to Y, and q can be the same as or different from n. Usually the group $-Y^*-SiR_qR''_{3-q}$ is the same as the group $-Y-SiR_nR''_{3-n}$, that is the secondary aminoalkylsilane has the formula $HN(-Y-SiR_nR''_{3-n})_2$. The secondary aminoalkylsilane can for example be $HN(CH_2)_3-Si(OC_2H_5)_3)_2$. The hydrolysable silane of the invention formed from such a secondary aminoalkylsilane with formaldehyde and an alcohol has the formula $R^3-Z-CH-N(-Y-SiR_nR''_{3-n})_2$. Such a hydrolysable silane has the advantage of a large number of hydrolysable groups R for bonding to a filler such as silica. The hydrolysable silane of the invention can for example be:

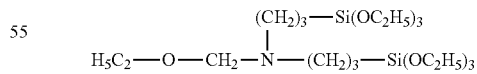

The secondary aminoalkylsilane can alternatively be a bis(secondary aminoalkylsilane) for example of the formula:

$$R_nR''_{3-n}Si-Y-(X-C(O)-CH2)m-NH-(CH_2)_d-$$
$$NH-(CH_2-C(O)-X'')_{m'}-Y^{**}-SiR_1R''_{3-r}$$

where R, R", n, Y, X and m are defined as above and d=1 to 8; $R^8$ represents hydrogen or a hydrocarbyl or substituted hydrocarbyl group having 1 to 8 carbon atoms; Z represents an oxygen or sulphur atom; $R^9$ represents a hydrocarbyl or substituted hydrocarbyl group having 1 to 20 carbon atoms;

X" represents —O— or NH—; m"=0 or 1; Y** represents a divalent organic spacer linkage having 1 to 20 carbon atoms; each R represents a hydrolysable group; each R" represents a hydrocarbyl group having 1 to 8 carbon atoms; and r=1 to 3. Reaction of such a secondary aminoalkylsilane with an aldehyde of the formula $R^2$—CHO and an alcohol of the formula $R^3$OH forms a hydrolysable silane of the invention having the formula:

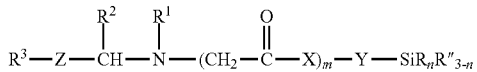

in which $R^1$ represents a group of the formula

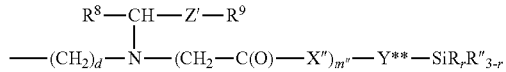

The secondary aminoalkylsilane can for example be of the formula $(C_2H_5O)_3Si$—$(CH_2)_3$—NH—$(CH_2)_d$—NH—$(CH_2)_3$—$Si(OC_2H_5)_3$ forming a hydrolysable silane of the invention having the formula:

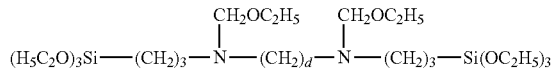

by reaction with formaldehyde and ethanol.

The group $R^1$ can alternatively be a carboxyalkyl ester group of the formula —$(CH_2)_e$—$C(O)OR^{10}$ wherein e=1 to 8; and $R^{10}$ represents a hydrocarbyl group having 1 to 8 carbon atoms, for example an ethyl carboxymethyl group or a methyl 3-carboxypropyl group. The secondary aminoalkylsilane can for example be of the formula $C_2H_5$—$C(O)O$—$CH_2$—NH—$(CH_2)_3$—$Si(OC_2H_5)_3$ forming a hydrolysable silane of the invention having the formula:

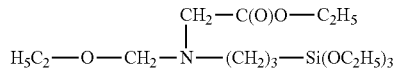

by reaction with formaldehyde and ethanol.

The alcohol of the formula $R^3$OH which is reacted with a secondary aminoalkylsilane and an aldehyde can alternatively be a group of the formula —$((CH2)_aO)_b$—$R^4$ wherein a=1 to 3; b=1 to 6; and $R^4$ represents hydrogen or a hydrocarbyl or substituted hydrocarbyl group having 1 to 20 carbon atoms. In this case the alcohol $R^3$OH is a diol such as ethylene glycol or propylene glycol, a polyoxyalkylene glycol such as polyoxyethylene glycol or polyoxypropylene glycol, an etheralcohol such as ethoxyethanol or methoxyethanol or a polyoxyalkylene glycol monoether such as ethoxyethoxyethanol.

When the alcohol $R^3$OH is an etheralcohol or a polyoxyalkylene glycol monoether, reaction with a secondary aminoalkylsilane of the formula $R^1$—NH—$(CH_2$—C—X)_m$—Y—$SiR_nR''_{3-n}$ and an aldehyde of the formula $R^2$—CHO forms a hydrolysable silane of the formula:

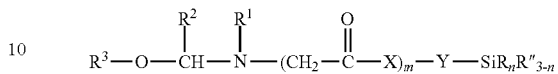

wherein $R^3$ represents an alkoxyalkyl group or poly(alkoxy)alkyl group. An example of such a hydrolysable silane is

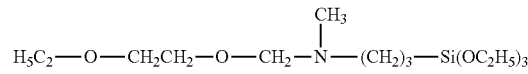

formed by reaction of ethoxyethanol with N-methyl-3-(triethoxysilyl)propylamine and formaldehyde.

When the alcohol $R^3$OH is a diol or a polyoxyalkylene glycol, reaction with a secondary aminoalkylsilane and an aldehyde can also form a bis(silylalkylaminoalkyl) ether by reaction of both alcohol groups of the diol or polyoxyalkylene glycol, if the diol or polyoxyalkylene glycol is used in stoichiometric excess. Reaction of a diol or polyoxyalkylene glycol of the formula —$((CH2)_aO)_b$—$R^4$ wherein a=1 to 3; b=1 to 6; and $R^4$ represents hydrogen with a secondary aminoalkylsilane of the formula $R^1$—N—$(CH_2$—C—X)_m$—Y—$SiR_nR''_{3-n}$ and an aldehyde of the formula $R^2$—CHO can form a bis(silylalkylaminoalkyl) ether of the formula:

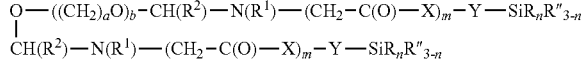

An example of such a bis(silylalkylaminoalkyl) ether is

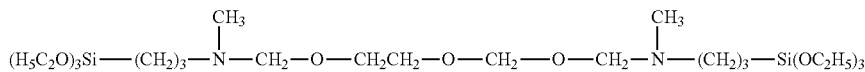

formed by the reaction of ethylene glycol with N-methyl-3-(triethoxysilyl)propylamine and formaldehyde. The reaction product of the diol or polyoxyalkylene glycol with the secondary aminoalkylsilane of the formula $R'$—N—$(CH_2$—C—X)_m$—Y—$SiR_nR''_{3-n}$ and the aldehyde of the formula $R^2$—CHO may be a mixture of a bis(silylalkylaminoalkyl) ether of the formula:

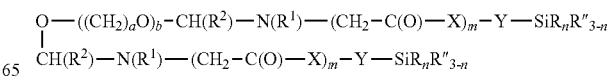

and a hydrolysable silane of the formula:

wherein $R^3$ represents a hydroxyalkyl group or poly(alkoxy) alkyl group of the formula $-((CH_2)_aO)_b-H$.

Preferably Z is Oxygen.

When Z is sulphur, that is when the reagent $R^3ZH$ is a thiol, the thiol is preferably not a simple alkylthiol since a malodorous alkylthiol may then be liberated during reaction with the C=C bonds present in diene elastomers upon heating to the temperatures used in elastomer processing. The group $R^3$ in a thiol $R^3SH$ preferably contains an anchoring group whereby any thiol liberated will remain chemically bound in the elastomer composition. Most preferably the group $R^3$ contains a hydrolysable silane group, since hydrolysable silane groups are capable of bonding strongly to fillers through hydrolysis of the silane group. $R^3$ can for example be a group of the formula $-Y''-SiR_pR''_{3-p}$ wherein Y'' represents a divalent organic spacer linkage having 1 to 20 carbon atoms; each R represents a hydrolysable group; each R'' represents a hydrocarbyl group having 1 to 8 carbon atoms; and p=1 to 3. The thiol can for example be $HS-(CH_2)_3-Si(OC_2H_5)_3$.

The thiol of the formula $HS-Y''-SiR_pR''_{3-p}$ can be reacted with a secondary aminoalkylsilane of the formula $R'-NH-(CH_2-C-X)_m-Y-SiR_nR''_{3-n}$ and an aldehyde of the formula $R^2-CHO$ to form a hydrolysable silane of the formula:

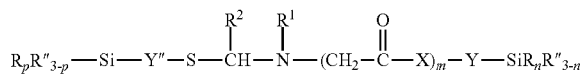

Examples of such hydrolysable silanes include

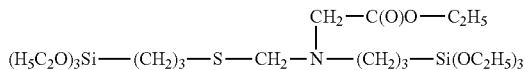

formed by the reaction of $HS-(CH_2)_3-Si(OC_2H_5)_3$ with $C_2H_5-C(O)O-CH_2-NH-(CH_2)_3-Si(OC_2H_5)_3$ and formaldehyde;

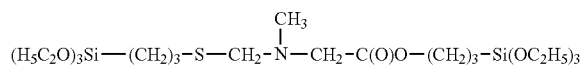

formed by the reaction of $HS-(CH_2)_3-Si(OC_2H_5)_3$ with $CH_3-NH-CH_2-C(O)O-(CH_2)_3-Si(OC_2H_5)_3$ and formaldehyde;

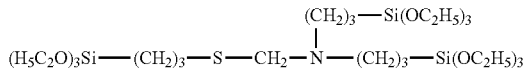

formed by the reaction of $HS-(CH_2)_3-Si(OC_2H_5)_3$ with $HN(CH_2)_3-Si(OC_2H_5)_3)_2$ and formaldehyde; and

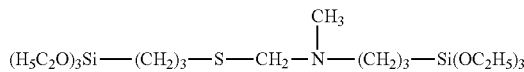

formed by the reaction of $HS-(CH_2)_3-Si(OC_2H_5)_3$ with $CH_3-NH-(CH_2)_3-Si(OC_2H_5)_3$ and formaldehyde.

The unsaturated silane can be partially hydrolysed and condensed into oligomers containing siloxane linkages. For most end uses it is preferred that such oligomers still contain at least one hydrolysable group bonded to Si per unsaturated silane monomer unit to enhance coupling of the unsaturated silane with fillers having surface hydroxyl groups.

The invention provides a hydrolysable silane according to claim 1, characterised in that Z represents an oxygen atom and R3 represents a hydrocarbyl group having 1 to 8 carbon atoms.

The invention provides a hydrolysable silane characterised in that Y represents a divalent organic spacer having 2 to 20 carbon atoms.

The invention provides a hydrolysable silane characterised in that Z represents an oxygen atom and R3 represents a group of the formula $-((CH2)aO)b-R4$ wherein a=1 to 3; b=1 to 6; and R4 represents hydrogen or a hydrocarbyl or substituted hydrocarbyl group having 1 to 20 carbon atoms.

The invention provides a hydrolysable silane characterised in that R4 represents hydrogen or a hydrocarbyl group having 1 to 8 carbon atoms.

The invention provides a hydrolysable silane, characterised in that R4 represents a group of the formula

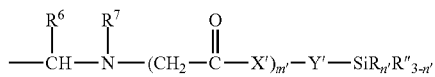

wherein R6 represents hydrogen or a hydrocarbyl or substituted hydrocarbyl group having 1 to 8 carbon atoms; R7 represents hydrogen or a hydrocarbyl or substituted hydrocarbyl group having 1 to 20 carbon atoms; X' represents $-O-$ or NH—; m'=0 or 1; Y' represents a divalent organic spacer linkage having 1 to 20 carbon atoms; each R represents a hydrolysable group; each R'' represents a hydrocarbyl group having 1 to 8 carbon atoms; and n'=1 to 3.

The invention provides a hydrolysable silane characterised in that Z represents a sulphur atom and R3 represents a group of the formula $-Y''-SiRpR''3-p$ wherein Y'' represents a divalent organic spacer linkage having 1 to 20 carbon atoms; each R represents a hydrolysable group; each R'' represents a hydrocarbyl group having 1 to 8 carbon atoms; and p=1 to 3.

The invention provides a hydrolysable silane characterised in that R1 represents a hydrocarbyl group having 1 to 8 carbon atoms.

The invention provides a hydrolysable silane characterised in that R1 represents a group of the formula $-Y^*-SiRqR''3-q$ wherein Y* represents a divalent organic spacer linkage having 1 to 20 carbon atoms; each R represents a hydrolysable group; each R'' represents a hydrocarbyl group having 1 to 8 carbon atoms; and q=1 to 3.

The invention provides a hydrolysable silane characterised in that R1 represents a group of the formula

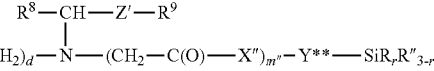

wherein d=1 to 8; $R^8$ represents hydrogen or a hydrocarbyl or substituted hydrocarbyl group having 1 to 8 carbon atoms; Z represents an oxygen or sulphur atom; $R^9$ represents a hydrocarbyl or substituted hydrocarbyl group having 1 to 20 carbon atoms; X" represents —O— or NH—; m"=0 or 1; Y** represents a divalent organic spacer linkage having 1 to 20 carbon atoms; each R represents a hydrolysable group; each R" represents a hydrocarbyl group having 1 to 8 carbon atoms; and r=1 to 3.

The invention provides a hydrolysable silane characterised in that R1 represents a group of the formula —(CH2)e-C(O)OR10 wherein e=1 to 8; and R10 represents a hydrocarbyl group having 1 to 8 carbon atoms.

The invention provides a hydrolysable silane characterised in that R2 represents hydrogen.

The invention provides a hydrolysable silane according characterised in that each group R is an alkoxy group having 1 to 4 carbon atoms.

The invention provides a hydrolysable silane characterised in that each group R is an ethoxy group.

The invention provides a hydrolysable silane characterised in that a=3.

The invention provides a hydrolysable silane characterised in that Y represents an alkylene group having 2 to 6 carbon atoms.

The invention provides a hydrolysable silane of the formulas:

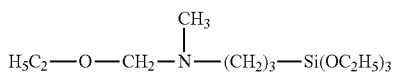

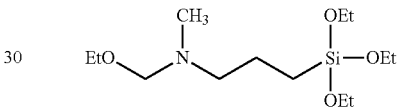

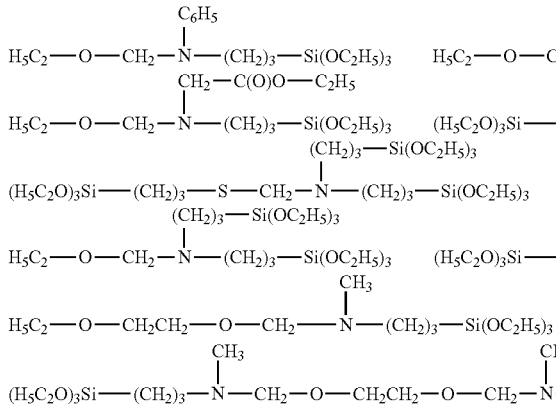

Preferably, the silane is partially hydrolysed and condensed into oligomers containing siloxane linkages.

The invention provides a process for the preparation of a hydrolysable silane of the formula

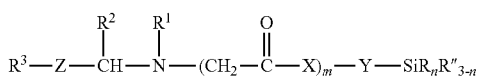

wherein each R represents a hydrolysable group; each R" represents a hydrocarbyl group having 1 to 8 carbon atoms; n=1 to 3; Y represents a divalent organic spacer linkage having 1 to 20 carbon atoms; X represents —O— or NH—; m=0 or 1; $R^1$ represents a hydrocarbyl or substituted hydrocarbyl group having 1 to 20 carbon atoms; $R^2$ represents hydrogen or a hydrocarbyl or substituted hydrocarbyl group having 1 to 8 carbon atoms; Z represents an oxygen or sulphur atom; and $R^3$ represents a hydrocarbyl or substituted hydrocarbyl group having 1 to 20 carbon atoms, characterised in that a secondary aminoalkylsilane of the formula R'—NH—(CH$_2$—C(O)—X)$_m$—Y—SiR$_n$R"$_{3-n}$ wherein R, R", n, Y, X and $R^1$ are defined as in claim 1, is reacted with an aldehyde of the formula $R^2$—CHO wherein $R^2$ represents hydrogen or a hydrocarbyl or substituted hydrocarbyl group having 1 to 8 carbon atoms and an alcohol or thiol of the formula $R^3$ZH wherein Z represents an oxygen or sulphur atom; and $R^3$ represents a hydrocarbyl or substituted hydrocarbyl group having 1 to 20 carbon atoms.

Preferably, the secondary aminoalkylsilane, the aldehyde and the alcohol or thiol are reacted at a temperature in the range 30 to 200° C., preferably 30 to 78° C. The reaction temperature is chosen so as to be lower or equal than the boiling point of the alcohol/thiol used (Methanol: 64.7° C., Ethanol: 78° C., 1-propanol: 97° C., Octanol: 196° C., Isopropanol: 82° C.).

Here follows examples for the preparation of hydrolysable silanes that are reactive towards diene elastomers.

EXAMPLE 1

Detailed synthesis of N-(ethoxymethyl)-N-(methyl)-3-aminopropyltriethoxysilane. A 1 L two necked round-bottom flask, fitted with a condenser, nitrogen sweep and magnetic stirrer was charged with 359.7 g of N-methyl-3-aminopropyltriethoxysilane, 45.87 g paraformaldehyde and 300 mL ethanol. The suspension was vigorously stirred and heated to 80° C. under nitrogen inert atmosphere. Ethanol reflux was maintained for less than 1 hour, until complete disappearance of solid particles in the reaction mixture before ethanol was removed in vacuo. Distillation allowed isolation of N-ethoxymethyl-N-methyl-3-aminopropyltriethoxysilane (87° C., 7*10$^{-2}$ mbar) from unreacted secondary amine, affording the alkoxymethylaminosilane with 90+ mol % purity and 20% yield. Both formation of the ethoxymethylamine structure and preservation of the triethoxysilane fragment were confirmed by nuclear magnetic resonance.

EXAMPLE 2

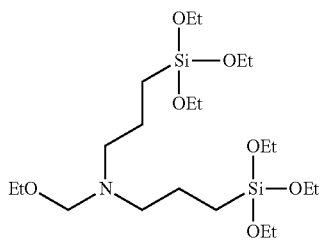 [SMILES: CCOCN(CCC[Si](OCC)(OCC)OCC)CCC[Si](OCC)(OCC)OCC]

Detailed synthesis of N-(ethoxymethyl)-N,N-bis(3-triethoxysilylpropyl)amine. A 1 L two necked round bottom flask, fitted with a condenser, nitrogen sweep and magnetic stirrer, was charged with 343.1 g of N,N-bis(3-triethoxysilylpropyl)amine, 24.2 g paraformaldehyde and 200 mL ethanol. The suspension was heated to 80° C. while stirring under nitrogen atmosphere. Ethanol reflux was maintained for less than 5 min, until complete disappearance of solid particles in the reaction mixture before ethanol was removed in vacuo. Final product was isolated with 99+% purity and 95% yield. Both formation of the ethoxymethylamine structure and preservation of the triethoxysilane fragment were confirmed by nuclear magnetic resonance.

EXAMPLE 3

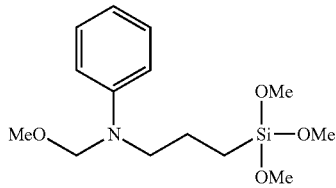 [SMILES: COCN(CCC[Si](OC)(OC)OC)c1ccccc1]

Detailed synthesis of N-(methoxymethyl)-N-phenyl-N-(3-trimethoxysilylpropyl)amine. A 250 ml two necked round bottom flask, fitted with a condenser, nitrogen sweep and magnetic stirrer, was charged with 44.1 g of N-phenyl-N-(3-trimethoxysilylpropyl)amine, 5.2 g paraformaldehyde and 35 ml methanol. The suspension was heated to 65° C. while stirring under nitrogen atmosphere. Methanol reflux was maintained for less than 1 hour, until complete disappearance of solid particles in the reaction mixture before methanol was removed in vacuo. Both formation of the methoxymethylamine structure and preservation of the trimethoxysilane fragment were confirmed by nuclear magnetic resonance. Prophetic examples from 4 to 10:

PROPHETIC EXAMPLE 4

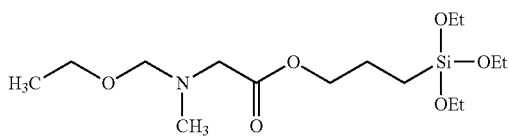 [SMILES: CCOCN(C)CC(=O)OCCC[Si](OCC)(OCC)OCC]

Detailed synthesis of N-(ethoxymethyl)-(3-triethoxysilylpropyl)sarcosinate. A 250 ml two necked round bottom flask, fitted with a condenser, nitrogen sweep and magnetic stirrer, will be charged with 44.0 g (3-triethoxysilylpropyl)sarcosinate, 4.5 g paraformaldehyde and 50 ml ethanol. The suspension will be heated to 80° C. while stirring under nitrogen atmosphere. Ethanol reflux will be maintained for less than 1 hour, until complete disappearance of solid particles in the reaction mixture before ethanol will be removed in vacuo. Wiped film distillation will allow isolation of N-(ethoxymethyl)-(3-triethoxysilylpropyl)sarcosinate from starting secondary amine. Both formation of the ethoxymethylamine structure and preservation of the triethoxysilane fragment will be verified by nuclear magnetic resonance.

PROPHETIC EXAMPLE 5

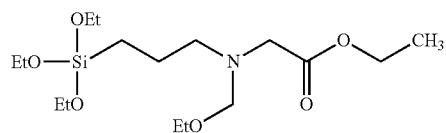 [SMILES: CCOCN(CCC[Si](OCC)(OCC)OCC)CC(=O)OCC]

Detailed synthesis of N-(ethoxymethyl)-N-(3-triethoxysilylpropyl) ethyl glycinate. A 250 ml two necked round bottom flask, fitted with a condenser, nitrogen sweep and magnetic stirrer, will be charged with 46.1 g N-(3-triethoxysilylpropyl) ethyl glycinate, 4.5 g paraformaldehyde and 50 ml ethanol. The suspension will be heated to 80° C. while stirring under nitrogen atmosphere. Ethanol reflux will be maintained for less than 1 hour, until complete disappearance of solid particles in the reaction mixture before ethanol will be removed in vacuo. Wiped film distillation will allow isolation of N-(ethoxymethyl)-N-(3-triethoxysilylpropyl) ethyl glycinate from starting secondary amine. Both formation of the ethoxymethylamine structure and preservation of the triethoxysilane fragment will be verified by nuclear magnetic resonance.

PROPHETIC EXAMPLE 6

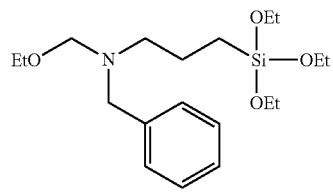 [SMILES: CCOCN(CCC[Si](OCC)(OCC)OCC)Cc1ccccc1]

Detailed synthesis of N-(ethoxymethyl)-N-benzyl-N-(3-triethoxysilylpropyl)amine. A 250 ml two necked round bottom flask, fitted with a condenser, nitrogen sweep and magnetic stirrer, will be charged with 46.7 g N-benzyl-N-(3-triethoxysilylpropyl)amine, 4.5 g paraformaldehyde and 50 ml ethanol. The suspension will be heated to 80° C. while stirring under nitrogen atmosphere. Ethanol reflux will be maintained for less than 1 hour, until complete disappearance of solid particles in the reaction mixture before ethanol will be removed in vacuo. Wiped film distillation will allow isolation of N-(ethoxymethyl)-N-benzyl-N-(3-triethoxysilylpropyl)amine from starting secondary amine. Both formation of the ethoxymethylamine structure and preservation of the triethoxysilane fragment will be verified by nuclear magnetic resonance.

PROPHETIC EXAMPLE 7

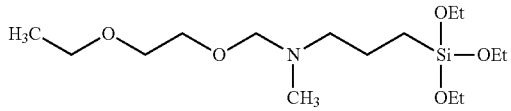

Detailed synthesis of N-(2-ethoxyethoxymethyl)-N-methyl-N-(3-triethoxysilylpropyl)amine. A 250 ml two necked round bottom flask, fitted with a condenser, nitrogen sweep and magnetic stirrer, will be charged with 35.3 g N-methyl-N-(3-triethoxysilylpropyl)amine, 4.5 g paraformaldehyde and 50 ml 2-ethoxyethanol. The suspension will be heated to 80° C. while stirring under nitrogen atmosphere. Heating reflux will be maintained for less than 1 hour, until complete disappearance of solid particles in the reaction mixture before 2-ethoxyethanol will be removed in vacuo. Wiped film distillation will allow isolation of N-(2-ethoxyethoxymethyl)-N-methyl-N-(3-triethoxysilylpropyl)amine from starting secondary amine. Both formation of the ethoxymethylamine structure and preservation of the triethoxysilane fragment will be verified by nuclear magnetic resonance.

PROPHETIC EXAMPLE 8

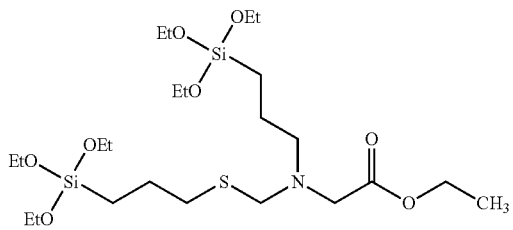 [SMILES: CCOC(=O)CN(CCC[Si](OCC)(OCC)OCC)CSCCC[Si](OCC)(OCC)OCC]

Detailed synthesis of N-(3-triethoxysilylpropyl)-N-(3-triethoxysilylpropylthiomethyl) ethyl glycinate. A 500 ml two necked round bottom flask, fitted with a condenser, nitrogen sweep and magnetic stirrer, will be charged with 61.5 g N-(3-triethoxysilylpropyl) ethyl glycinate, 6.0 g paraformaldehyde and 50 ml toluene. The mixture will be refluxed for 3 h 40 and formed water will be removed using a Dean-Stark set-up. Then, 47.7 g triethoxy(3-mercaptopropyl)silane will be added and reflux will be maintained for 1 additional hour. N,N-bis(3-triethoxysilylpropyl)-N-(3-triethoxysilylpropylthiomethyl)amine will be purified by filtration of solids through paper filter followed by evaporation of volatiles in vacuo. Both formation of the thiomethylamine structure and preservation of the triethoxysilane fragment will be confirmed by nuclear magnetic resonance.

PROPHETIC EXAMPLE 9

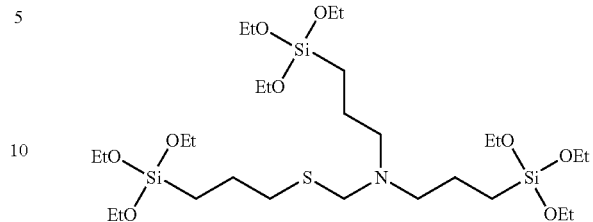

Detailed synthesis of N,N-bis(3-triethoxysilylpropyl)-N-(3-triethoxysilylpropylthiomethyl)amine. A 500 ml two necked round bottom flask, fitted with a condenser, nitrogen sweep and magnetic stirrer, was charged with 85.2 g N,N-bis(3-triethoxysilylpropyl)amine, 6.0 g paraformaldehyde and 50 ml toluene. The mixture was refluxed for 3 h 40 and formed water was removed using a Dean-Stark set-up. Then, 47.7 g triethoxy(3-mercaptopropyl)silane was added and reflux maintained for 1 additional hour. N,N-bis(3-triethoxysilylpropyl)-N-(3-triethoxysilylpropylthiomethyl)amine was isolated by filtration of solids through paper filter followed by evaporation of volatile impurities in vacuo (100° C., 10 mbar). Purity level was 73% and yield 92%. Both formation of the thiomethylamine structure and preservation of the triethoxysilane fragment was confirmed by nuclear magnetic resonance.

PROPHETIC EXAMPLE 10

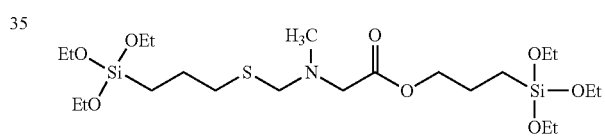

Detailed synthesis of N-(3-triethoxysilylpropylthiomethyl)-(3-troethoxysilylpropyl)sarcosinate. A 500 ml two necked round bottom flask, fitted with a condenser, nitrogen sweep and magnetic stirrer, will be charged with 61.5 g (3-triethoxysilylpropyl)sarcosinate, 6.0 g paraformaldehyde and 50 ml toluene. The mixture will be refluxed for 3 h 40 and formed water will be removed using a Dean-Stark set-up. Then, 47.7 g triethoxy(3-mercaptopropyl)silane will be added and reflux will be maintained for 1 additional hour. N-(3-triethoxysilylpropylthiomethyl)-(3-troethoxysilylpropyl)sarcosinate will be purified by filtration of solids through paper filter followed by evaporation of volatile impurities in vacuo (100° C., 10 mbar). Both formation of the thiomethylamine structure and preservation of the triethoxysilane fragment will be confirmed by nuclear magnetic resonance.

The invention claimed is:
1. A hydrolysable silane of the formula

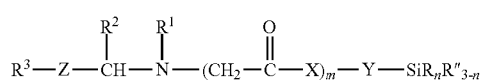

wherein each R represents a hydrolysable group; each R″ represents a hydrocarbyl group having 1 to 8 carbon atoms; n=1 to 3; Y represents a divalent organic spacer linkage having 2 to 20 carbon atoms; X represents —O— or —NH—; m=0 or 1; $R^2$ represents hydrogen or a hydrocarbyl or substituted hydrocarbyl group having 1 to 8 carbon atoms;

and comprising at least one of the following limitations 1) through 6):

1) Z represents an oxygen atom, $R^1$ represents a hydrocarbyl or substituted hydrocarbyl group having 1 to 20 carbon atoms, $R^3$ represents a group of the formula —$((CH_2)_aO)_b$—$R^4$ wherein a=1 to 3; b=1 to 6; and $R^4$ represents hydrogen or a hydrocarbyl or substituted hydrocarbyl group having 1 to 20 carbon atoms;

2) Z represents a sulphur atom, $R^1$ represents a hydrocarbyl or substituted hydrocarbyl group having 1 to 20 carbon atoms and $R^3$ represents a group of the formula —Y"—$SiR_pR"_{3-p}$ wherein Y" represents a divalent organic spacer linkage having 1 to 20 carbon atoms; and p=1 to 3;

3) Z represents an oxygen or a sulphur atom; $R^1$ represents a group of the formula —Y*—$SiR_qR"_{3-q}$ wherein Y* represents a divalent organic spacer linkage having 1 to 20 carbon atoms; q =1 to 3; and $R^3$ represents a hydrocarbyl or substituted hydrocarbyl group having 1 to 20 carbon atoms, provided that when $R^3$ is $CH_3$;

4) $R^1$ represents a group of the formula

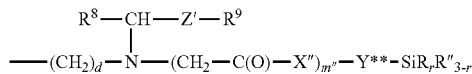

wherein d =1 to 8; $R^8$ represents hydrogen or a hydrocarbyl or substituted hydrocarbyl group having 1 to 8 carbon atoms; Z and Z' independently represent an oxygen or sulphur atom; $R^9$ represents a hydrocarbyl or substituted hydrocarbyl group having 1 to 20 carbon atoms; X" represents —O— or —NH—; m"=0 or 1; Y** represents a divalent organic spacer linkage having 1 to 20 carbon atoms; r =1 to 3; and $R^3$ represents a hydrocarbyl or substituted hydrocarbyl group having 1 to 20 carbon atoms;

5) $R^1$ represents a group of the formula —$(CH_2)_e$—C(O)$OR^{10}$ wherein e=1 to 8; $R^{10}$ represents a hydrocarbyl group having 1 to 8 carbon atoms; and Z represents an oxygen or sulphur atom; $R^3$ represents a hydrocarbyl or substituted hydrocarbyl group having 1 to 20 carbon atoms; or 6) Z represents an oxygen atom, $R^1$ represents a hydrocarbyl group having 1 to 20 carbon atoms, $R^3$ represents a hydrocarbyl or substituted hydrocarbyl group having from 1 to 20 carbon atoms.

2. A hydrolysable silane according to Claim 1, comprising limitation 1) wherein $R^4$ represents hydrogen or a hydrocarbyl group having 1 to 8 carbon atoms.

3. A hydrolysable silane according to Claim 1, comprising limitation 1) wherein $R^4$ represents a group of the formula

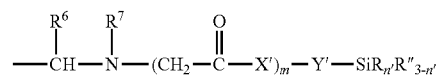

wherein R6 represents hydrogen or a hydrocarbyl or substituted hydrocarbyl group having 1 to 8 carbon atoms; $R^7$ represents hydrogen or a hydrocarbyl or substituted hydrocarbyl group having 1 to 20 carbon atoms; X' represents —O— or —NH—; m'=0 or 1; Y' represents a divalent organic spacer linkage having 1 to 20 carbon atoms; each R represents a hydrolysable group; each R" represents a hydrocarbyl group having 1 to 8 carbon atoms; and n'=1 to 3.

4. A hydrolysable silane according to claim 1, comprising at least one of limitations 1), 2), or 6) wherein $R^1$ represents a hydrocarbyl group having 1 to 8 carbon atoms.

5. A hydrolysable silane according to claim 1, characterised in that $R^2$ represents hydrogen or each R group is an alkoxy group having 1 to 4 carbon atoms.

6. A hydrolysable silane according to claim 5, characterised in that each R group is an ethoxy group.

7. A hydrolysable silane according to claim 1, characterised in that n=3.

8. A hydrolysable silane according to claim 1, characterised in that Y represents an alkylene group having 2 to 6 carbon atoms.

9. The hydrolysable silane of the formula

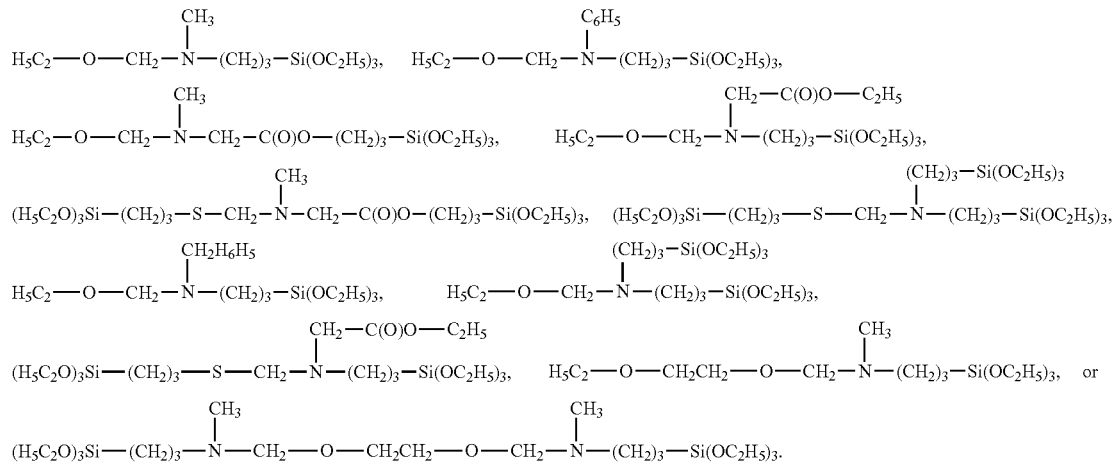

10. A hydrolysable silane according to claim 1, wherein the silane is partially hydrolysed and condensed into oligomers containing siloxane linkages.

11. A process for the preparation of a hydrolysable silane of the formula

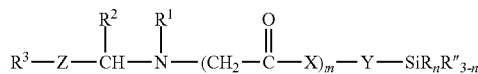

wherein each R represents a hydrolysable group; each R" represents a hydrocarbyl group having 1 to 8 carbon atoms; n=1 to 3; Y represents a divalent organic spacer linkage having 1 to 20 carbon atoms; X represents —O— or —NH—; m=0 or 1; $R^1$ represents a hydrocarbyl or substituted hydrocarbyl group having 1 to 20 carbon atoms; $R^2$ represents hydrogen or a hydrocarbyl or substituted hydrocarbyl group having 1 to 8 carbon atoms; Z represents an oxygen or sulphur atom; and $R^3$ represents a hydrocarbyl or substituted hydrocarbyl group having 1 to 20 carbon atoms, characterised in that a secondary aminoalkylsilane of the formula $R^1$—NH—(CH$_2$—C(O)—X)$_m$—Y—SiR$_n$R"$_{3-n}$, wherein R, R", n, Y, X and $R^1$ are defined as in claim 1, is reacted with an aldehyde of the formula $R^2$—CHO wherein $R^2$ represents hydrogen or a hydrocarbyl or substituted hydrocarbyl group having 1 to 8 carbon atoms and an alcohol or thiol of the formula $R^3$ZH wherein Z represents an oxygen or sulphur atom; and $R^3$ represents a hydrocarbyl or substituted hydrocarbyl group having 1 to 20 carbon atoms.

12. A process according to claim 11 characterised in that the secondary aminoalkylsilane, the aldehyde and the alcohol or thiol are reacted at a temperature in the range 30 to 200° C.

* * * * *